United States Patent [19]

Vanderpool et al.

[11] Patent Number: 4,757,143

[45] Date of Patent: Jul. 12, 1988

[54] CATALYTIC METHOD FOR THE MANUFACTURE OF TRIETHYLENEDIAMINE

[75] Inventors: Steven H. Vanderpool, New Braunfels; Walter H. Brader, Jr., Austin; Ernest L. Yeakey, Austin; Edward C. Nieh, Austin; Thomas T. McConnell, Austin, all of Tex.

[73] Assignee: Texaco Inc., White Plains, N.Y.

[21] Appl. No.: 871,939

[22] Filed: Jun. 9, 1986

[51] Int. Cl.[4] .................. C07D 487/08; C07D 295/02; C07B 35/10

[52] U.S. Cl. .................................... 544/352; 544/351; 544/404; 544/358

[58] Field of Search ................................ 544/352, 351

[56] References Cited

U.S. PATENT DOCUMENTS

| | | | |
|---|---|---|---|
| 3,285,920 | 11/1966 | Muhlbauer | 544/352 |
| 4,588,842 | 5/1986 | Vanderpool | 564/479 |
| 4,647,664 | 3/1987 | Vanderpool | 544/178 |

*Primary Examiner*—Mark L. Berch
*Attorney, Agent, or Firm*—Jack H. Park; Kenneth R. Priem; Carl G. Ries

[57] ABSTRACT

Cyclic and acyclic hydroxyethyl ethylenepolyamines are converted to triethylenediamine when using a catalyst composed of zirconia or titania to which from about 0.5 to about 7 wt. % of phosphorous has been thermally chemically bonded in the form of phosphate linkages.

12 Claims, No Drawings

CATALYTIC METHOD FOR THE MANUFACTURE OF TRIETHYLENEDIAMINE

BACKGROUND OF THE INVENTION

1. Field of the Invention

This invention relates to a catalytic method for the preparation of diazabicyclo-(2.2.2.)-octane (triethylenediamine). More particularly, this invention relates to a catalytic method for the manufacture of triethylenediamine from hydroxyethyl derivatives of cyclic and acyclic. Still more particularly, this invention is directed to the use of titania and zirconia catalysts to which a minor amount of phosphorus has been thermally chemically bonded at the surface thereof in the form of phosphate linkages. Even more particularly, the present invention is directed a continuous process for the manufacture of triethylenediamine from hydroxyethyl derivatives of cyclic and acyclic ethylenepolyamines by passing such feedstocks over a bed of catalyst in a reaction zone wherein the catalyst is composed of pellets of titania and/or zirconia to which a minor amount of phosphorus (0.5 to 7 wt. %) has been thermally chemically bonded to the surface in the form of phosphate linkages.

2. Prior Art

The catalysts used in the practice of the process of the present invention are disclosed in Vanderpool U.S. Pat. No. 4,588,842, a division of abandoned Vanderpool U.S. application Ser. No. 455,160, filed Jan. 3, 1983, upon which is based European patent application Ser. No. 83,307,520.3 published Aug. 28, 1984, wherein they are disclosed as useful in promoting the reaction of ethylenediamine with ethanolamine to provide essentially linear polyethylenepolyamine reaction products. Minor quantities of cyclic products are also formed.

It has heretofore been proposed to manufacture triethylenediamine from a wide variety of cyclic and acyclic polyethylenepolyamines. For example, it has been proposed to use solid cracking catalysts such as silica-alumina cracking catalysts to manufacture triethylenediamine from feedstocks such as polyethylenepolyamines (Herrick U.S. Pat. No. 2,937,176), from mixtures of diethanolamine with ethylenediamine (Mascioll U.S. Pat. No. 2,977,364), from N-aminoethyl piperazine (Krause U.S. Pat. No. 2,985,658), and from mixed feedstocks such as a feedstock containing both cyclic and acyclic polyethylenepolyamines such as N-aminoethyl piperazine and hydroxyethyl piperazine, diethylenetriamine and aminoethylethanolamine (Brader et al. U.S. Pat. No. 3,231,573). Brader U.S. Pat. No. 3,157,657 discloses the preparation of triethylenediamine from N-aminoethyl piperazine using a catalyst comprising tungsten or a base modified silica alumina cracking catalyst (Brader U.S. Pat. No. 3,120,526). U.S. Pat. No. 3,080,371 discloses the use of an organic carboxylic acid to catalyze the conversion of hydroxyethyl piperazine to triethylenediamine.

Brader et al. U.S. Pat. No. 3,297,701 discloses a method for the preparation of triethylenediamine by bringing an appropriate feedstock such as a cyclic or acyclic polyethylenepolyamine (e.g., N-aminoethyl piperazine, monoethanolamine, etc.) into contact with a phosphate of an enumerated metal (e.g., aluminum, calcium or iron phosphate). Also, Brader et al. propose the use of 2-(2-hydroxyethoxy)ethylamine as a feedstock for the synthesis of triethylenediamine in U.S. Pat. No. 3,172,891 using an aluminum phosphate catalyst.

Muhlbauer et al. U.S. Pat. No. 3,285,920 is directed to a continuous process for the manufacture of piperazine and triethylenediamine wherein N-aminoethyl piperazine is converted to triethylenediamine using a silica-alumina cracking catalyst alone or modified with alkaline earth metal oxides, alkali metal oxides, zirconia, etc., a tungsten catalyst or a phosphate salt such as a phosphate salt of aluminum or iron.

In Wells U.S. Pat. No. 4,405,784, a method for the manufacture of triethylenediamine from a cyclic or acyclic polyethylenepolyamine is discloses wherein the catalyst that is used is strontium diorthophosphate.

SUMMARY OF INVENTION

It has been surprisingly discovered in accordance with the present invention that hydroxyethyl derivatives of cyclic and acyclic ethylenepolyamines may be converted to triethylenediamine (TEDA) with excellent yields and excellent selectivities when using a catalyst composed of zirconia or titania to which from about 0.5 to about 7 wt. % of phosphorus has been thermally chemically bonded in the form of phosphate linkages.

DETAILED DESCRIPTION OF THE EMBODIMENT

Feedstocks

The hydroxyethyl derivatives of cyclic and acyclic ethylenepolyamines that may be used as feedstocks in accordance with the present invention include feedstocks having the formula:

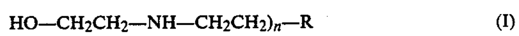

$$HO-CH_2CH_2-NH-CH_2CH_2)_n-R \quad (I)$$

wherein R represents —OH or —$NH_2$ and n is an integer having a value of 1 to 2.

Another class of materials that may be used as feedstocks include cyclic ethylenepolyamines characterized by the following formula:

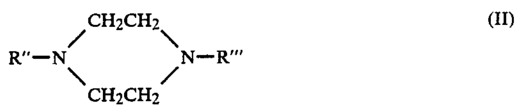

wherein R'' represents —$CH_2CH_2OH$ and R''' represents —$CH_2CH_2OH$ or H.

Representative members of this class include compounds such as N-hydroxyethylpiperazine and bis-N-hydroxyethylpiperazine.

Hydroxy terminated derivates of the foregoing materials may also be used as feedstocks in accordance with the present invention, such feedstocks being prepared by ethoxylating a cyclic or an acyclic polyethylenepolyamine having Formula I or II (where R'' and R''' equal H), above, or a mixture of such amines with from about 0.5 to about 1.5 mole equivalents of ethylene oxide per mole of amine.

Catalysts

The pelleted catalyst compositions of the present invention are normally employed as a fixed bed of catalyst in a continuous reaction system. In a continuous process of this nature, the time of contact of the reactants with the catalyst is one of the interrelated factors that those skilled in the art will adjust, along with temperature, pressure, bed geometry, pellet size, etc. in order to obtain a desired rate of reaction and, hence a desired percentage of conversion of the reactants. In a continuous process, it is not necessary to drive the reaction to completion because unreacted feedstock components can be recycled to the reactor.

It is customary to use cylindrically-shaped catalyst pellets having a diameter essentially equal to the length thereof, such as diameters and lengths ranging from about 0.794 mm (1/32 inch) to about 9.525 mm (⅜ inch). It will be understood that the shape and dimensions of the pellets are not critical to the present invention and that pellets of any suitable shape and dimensions may be used, as desired, by one wishing to practice the process of the present invention.

When cylindrical pellets of catalyst of the type described above are used, the weighted hourly space velocity may be varied within wide limits (e.g., 0.1 to 5 w/hr/w) in order to obtain a desired rate of conversion, as explained above. Normally, space velocities of about 0.5 to 2 w/hr/w will be employed.

Catalyst life is an important factor in conducting a continuous reaction. For example, if a catalyst is easily poisoned, or if catalyst pellets do not have good structural properties, the economics of the process will be seriously and adversely affected.

The catalysts of the present invention are not particularly susceptible to poisoning so this normally does not present a problem. However, under the reaction conditions employed, amines of the type used and formed herein have the potential capability of leaching or otherwise adversely affecting the structural integrity of the pellets. In an extreme instance, catalyst pellets having good initial crush strength and surface hardness will be reduced to fines very rapidly when used under reaction conditions such as those employed herein.

The pelleted catalyst compositions of the present invention are advantageously used in a continuous process for the continuous production of TEDA from cyclic and acyclic polyethylene polyamines and hydroxy terminated derivatives thereof. As shown herein, such catalyst compositions can be used for prolonged periods without the need for regeneration. Nevertheless, with the passage of time deactivation will tend to slowly occur. Deactivation can be measured qualitatively as the increase of temperature required to maintain an essentially constant conversion rate.

When a catalyst composition of the present invention has become deactivated, or at least partially deactivated, in the sense that the temperature required to maintain a desired conversion level is considered to be excessive, the catalyst may be regenerated with ease with oxygen under controlled regeneration conditions as disclosed in Vanderpool U.S. Pat. No. 4,540,822.

The regeneration temperature is preferably within the range of about 350° to about 550° C. and more preferably within the range of 400° to 500° C. The oxygen is used in concentrations of 1 to 20%, the balance being an inert gas such as nitrogen, flue gas, etc.

In accordance with the preferred procedure the regeneration is initiated with a mixture of oxygen and inert gas containing from about 1 to about 3% oxygen, the balance being the inert gas. This mixture of oxygen and inert gas is passed through the catalyst bed at an initially comparatively moderate temperature of about 350° to about 450° C., and more preferably from about 400° to about 450° C. This may be considered as a preconditioning step and should be continued for a length of time within the range of about 0.5 to about 5 hours, such as a period of one to two hours. Thereafter the oxygen concentration can be progressively increased or increased in stages to a concentration of from about 3% to about 20% oxygen while increasing the temperature, if desired, to a temperature within the range of about 400° to 550° C., such as a temperature within the range of about 450° to 500° C. The oxygen treatment may be continued in this fashion suitably for about 2 to 10 hours. Thereafter the catalyst bed is flushed with an inert gas until it is cooled and it may then be restored to service.

The catalyst compositions of the present invention are prepared by depositing a phosphorus compound on titania or zirconia, as described in greater detail in copending Vanderpool application Ser. No. 06/564,153 filed Dec. 22, 1983, now U.S. Pat. No. 4,588,842, and entitled "Catalytic Preparation of Linear Polyethylenepolyamines" and in said Vanderpool European patent application Ser. No. 307,520.3 published Aug. 28. 1984. Pellets of titania or zirconia may be prepared by extrusion or by compaction in conventional pelleting apparatus using a pelleting aid such as graphite. It is also within the scope of the present invention to deposit the phosphorus compound on powdered titania or zirconia followed by pelleting and calcination.

Any appropriate water soluble or liquid phosphorus compound can be used as a source of the phosphorus. For convenience, phosphoric acid will normally be used. However, other phosphorus compounds such as phosphoryl chloride ($POCl_3$), phosphorous acid, polyphosphoric acid, phosphorus halides, such as phosphorus bromide, alkyl phosphates and alkyl phosphites such as trimethyl phosphate, triethyl phosphate, trimethyl phosphite, triethyl phosphite, etc. may be utilized. Also, a diamminohydrogen phosphate such as diammonium hydrogen phosphate, $(NH_4)_2HPO_4$, dimethylamino hydrogen phosphate, $(CH_3)_2NH_2PO_4$, diethylaminohydrogen phosphate $(CH_3CH_2)_2NH_2PO_4$, etc. may be used.

As a matter of convenience, the normal practice is to use only one chemical as a phosphorus source (e.g., aqueous phosphoric acid). However, mixtures of two or more such reagents may be used if desired.

Preferably the catalyst composition is prepared by impregnating a preformed pellet. A suitable procedure to be used is to heat the water soluble or liquid phosphorus compound at a temperature of about 100° to about 150° C. and to then add pellets in an amount about equal to the volume of the heated liquid. This treatment should be continued from about 0.5 to about 5 hours. At the end of that time, the resulting mixture of pellets and liquid is cooled, decanted to remove excess liquid followed by washing with an amount of water adequate to substantially completely remove unadsorbed liquid. Temperatures above 150° C. can be used, if desired, but there is no particular advantage in doing so.

It will be understood that the phosphorus that is present on a thus-treated pellet is not present as elemental phosphorus, but rather as phosphorus that is chemically bound, probably as an oxide, to the titania or zirconia support. This is demonstrated by the fact that repeated washing will not remove all of the phosphorus. However, the exact nature of the bonding is not completely understood.

The amount of phosphorus that is bonded to the support is a function of heating and other conditions used in the treating step and is also a function of the chemical identity of the phosphorus compound that is used as a source of phosphorus. Under the treating conditions exemplified above, at least about 0.5 wt % of phosphorus is caused to bond (i.e., permanently adhere) to the pellets. There is an upper limit to the amount of phosphorus that bonds to the support. This upper limit is, as indicated, a function of both the treating conditions and the chemical used as a source of the phosphorus. Normally, the maximum amount of phosphorus that can be caused to bond to the pellets is about 7 wt. %.

When the pellets are impregnated with the phosphorus compound at a temperature of at least about 100° C., there is no absolute need to calcine the catalyst composition before use. However, the pellets can be calcined prior to use, if desired, as a precautionary measure and/or in order to still further improve the physical properties of the pellets. The pellets are suitably calcined at a temperature of about 200° C. to about 800° C. for a period of time within the range of 2 to 24 hours; more preferably at a temperature of about 300° C. to about 600° C. for about 4 to 16 hours.

Other procedures can be used in adding phosphorus to the titania or zirconia. For example, the pellets can be treated with the phosphorus compound at ambient temperatures or at more modest elevated temperatures of less than about 100° C. However, the catalyst should be calcined as described above without washing.

Alternatively, the titania or zirconia can be treated with the phosphorus-containing compound in powdered form and the powder can thereafter be pelleted. If the treatment is conducted at a temperature of about 100° C. or more, thermal activation will normally have been obtained and it will not be absolutely necessary to perform a calcining operation prior to use. If lower treating temperatures are used, calcining prior to use is normally a desired operation. The calcining operation can be conducted prior to or subsequent to the pelleting step. Any appropriate pelleting procedure of the type known to those skilled in the art may be used. For example, the treated powdered titania or zirconia can be mixed with graphite and/or other binders and compacted or extruded under conventional conditions.

In any event, in-situ calcining will occur when the pelleted catalyst compositions are used to catalyze the reaction of the cyclic and/or acyclic polyethylenepolyamine and/or hydroxy terminated derivative feedstock at 300° to 400° C. to at least partially convert the feedstock to TEDA, as is hereinafter more fully set forth.

Reaction Conditions

The reaction of the present invention is conducted utilizing a feedstock of the present invention which is dissolved in water so as to form about a 5 to about 50 wt. % aqueous solution of feedstock, such as a 20 wt. % aqueous solution, which is brought into contact with a catalyst in a batch reactor or in a continuous reactor.

When the reaction is conducted in a batch reactor, the catalyst will preferably be employed in powdered form, whereas when the reaction is conducted on a continuous basis the catalyst is preferably employed in the form of pellets.

The reaction is suitably conducted at a temperature of about 250°-400° C. and, more preferably, at a temperature of about 300° to about 350° C.

The reaction is also preferably conducted at atmospheric pressure. Superatmospheric or subatmospheric pressures may be utilized if desired, but there is no particular advantage in doing so.

When the reaction is conducted on a batch basis, the reaction time may suitably vary from about 1 to about 5 hours. When the reaction is conducted on a continuous basis, the feedstock may suitably be passed over a bed of pelleted catalyst at a liquid hourly space velocity (lhsv) of about 0.1 to about 10 volumes of the aqueous solution of the amine feedstock per volume of catalyst per hour. More preferably, the lhsv will be from about 0.5 to about 2.

It is not necessary to use either ammonia or hydrogen as feed components in the practice of the process of the present invention.

Recovery and Purification

The product of the present invention, triethylenediamine, is a compound having the formula:

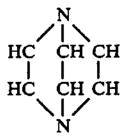

(III)

Triethylenediamine in its pure form is a hygroscopic crystalline solid having a melting point of about 158°-160° C. Triethylenediamine is sparingly soluble in glycols such as ethylene glycol, propylene glycol, diethylene glycol, dipropylene glycol, etc. Also, when an aqueous reaction product containing triethylenediamine and propylene glycol is distilled, the triethylene diamine and propylene glycol can be distilled overhead as a triethylene diamine-propylene glycol azeotrope, thereby resulting in the recovery of a purified material in liquid form. This has the advantage of avoiding the necessity of recovering the triethylenediamine as a hygroscopic crystalline solid with all of the processing problems that are entailed in the handling of hygroscopic crystalline solids.

EXAMPLES

I. Equipment and Procedures

In all cases, these evaluations were performed in a 100 cc reactor constructed of ¾ inch stainless steel tubing connected to ⅛ inch feed and effluent lines with swagelok fittings. The reactor tube was situated inside of a 3×3 inch aluminum block which was heated electrically with four 1000 watt strip heaters. Temperature control was achieved with a Thermoelectric controller monitoring thermocouples attached to the skin of the reactor body. The feed was charged to the reactor system with a Beckman 110A L.C. pump. For safety, pressure relief was provided by a 3000 lb. rupture disk assembly although all runs were preformed at atmospheric pressure to minimize bimolecular reactions. The reactor effluent was collected in a glass jug and sampled after the system had lined-out at the proscribed temperature for at least 2.5 hours.

In general the feedstock consisted of a 4:1 aqueous feed. For example, HEP feed consisted of 4 parts water by weight and 1 part HEP by weight. For the runs using nitrogen as a diluent, a different feed system was used; this will be described in detail hereinafter.

The catalyst that was used was prepared from pelleted titania and polyphosphoric acid. It had about 2 wt. % of phosphorus thermally chemically bonded thereto and was prepared by dipping the preformed pellets into a 30% polyphosphoric acid solution, followed by decanting and calcining at 450° C.

Analysis of the reactor effluent was achieved using an OV-17 column in a Hewlett-Packard 5710A gas chromatograph. Analysis was on a water-free and feed-free basis. Since the conversion of HEP and BisHEP were nearly quantitative, the selectivities were close to calculated yields.

Screening Reactions

A. N-Hydroxyethyl Piperazine (HEP) Feedstock

1. Aqueous Feedstock Water Diluent

As described above, a 20 wt. % aqueous HEP solution was charged to the reactor with the results shown below. In this experiment, the purpose of the water is to further minimize bimolecular reactions that would be expected to result in the dimerization and polymerization of the HEP by acting as an inert diluent. In larger reactor systems water may be necessary as a heat transport medium. It must be emphasized that these selectivities are only approximate due to the nature of G.C. analysis.

Data is presented in Table I.

TABLE I[a]

| | | TEDA via HEP | | | | |
|---|---|---|---|---|---|---|
| Ex. | TEMP[b] | Conv. | TEDA | PIP | EtPIP | Hvs[c] |
| 1 | 298 | 36 | 66 | 3.6 | 1.3 | 15 |
| 2 | 311 | 86 | 83 | 4.2 | 3.4 | 7 |
| 3 | 320 | 100 | 88 | 5.8 | 6.0 | <1 |
| 4 | 330 | 100 | 83 | 7.1 | 9.3 | <1 |
| 5 | 337 | 100 | 75 | 8.0 | 13.6 | <1 |

[a]Data is basis GC analysis of crude reactor effluents. Selectivities are approximate Area % on a water and feed free basis.
[b]Temperature in degrees Centigrade.
[c]Heavies are probably dimers of HEP.

The obvious interpretations are:

1. Increased temperatures increase byproduct formation and result in further reaction of an unidentified heavy by-product to give additional TEDA, piperazine and N-ethylpiperazine.
2. Selectivity to the desired TEDA is optimized at the minimum temperature required for 100% HEP conversion.
3. The heavy byproducts are apparently convertible to TEDA.

2. Mass Balance

The above process was run overnight using the equipment and procedures described in I for a material balance evaluation. A 99% mass balance was achieved across the reactor. The reactor effluent (obtained at 320° C.) was about 14% TEDA or about 81% molar yield. This effluent was distilled in the presence of propylene glycol. A recovered molar yield of 74% was obtained.

In particular, 1868 g of effluent was obtained which contained about 257 g TEDA. This value was obtained by G.C. analysis using a correction factor obtained from a standard containing about 15% TEDA in water. 600 g of propylene glycol was added to the reactor effluent before distillation to create a TEDA/PG azeotrope thereby eliminating the distillation of solid TEDA. The TEDA/PG azeotrope has a 1:2 weight ratio. 600 g PG was used to give about 20% excess and assure a liquid overhead.

| Mass Balance Distillation | | |
|---|---|---|
| Cut 1 to 185° C. | Very little TEDA | 5 g |
| Cut 2 185–188° C. | PG with some TEDA | 10 g |
| Cut 3 188–191° C. | 33% TEDA in PG | 202 g |
| Btms | Some TEDA | 5 g |
| Column holdup | | 15 g |
| Total | | 237 g |

B. Crude HEP Feedstock

The feedstocks discussed below were prepared in a high pressure laboratory by digesting the required amount of ethyleneoxide (EO) in an aqueous solution of piperazine (PIP) at 90°–100° C. for 2 hours. The organics were diluted to a 20 wt. % solution with distilled water and runs were made using the equipment and procedures of I. G.C. analysis of the crude reactor effluents are provided in Table II.

TABLE II[a]

| | | | TEDA via Crude HEP | | | | |
|---|---|---|---|---|---|---|---|
| | | | Conv. (%) | | Select. (%) | | |
| Ex. | Adduct[b] | TEMP[c] | HEP | BisHEP | TEDA | PIP | EtPIP |
| 6 | 0.5:1 | 290 | 54 | 59 | 78 | 20 | — |
| 7 | " | 296 | 72 | — | 78 | 20 | — |
| 8 | " | 300 | 76 | 79 | 78 | 19 | 1 |
| 9 | " | 306 | 88 | 100 | 79 | 18 | 1 |
| 10 | " | 310 | 92 | 100 | 78 | 15 | 2 |
| 11 | " | 315 | 97 | 100 | 77 | 16 | 2 |
| 12 | " | 320 | 99 | 100 | 77 | 14 | 3 |
| 13 | " | 325 | 100 | 100 | 76 | 10 | 4 |
| 14 | 1:1 | 291 | 50 | 65 | 91 | 7 | 1 |
| 15 | " | 300 | 66 | 79 | 89 | 8 | 1 |
| 16 | " | 305 | 79 | 91 | 89 | 7 | 1 |
| 17 | " | 310 | 87 | 95 | 86 | 6 | 2 |
| 18 | " | 315 | 95 | 100 | 84 | 9 | 2 |
| 19 | " | 320 | 98 | 100 | 80 | 10 | 3 |
| 20 | " | 324 | 99 | 100 | 81 | 10 | 4 |
| 21 | 1.5:1 | 300 | 74 | 88 | 92 | 3 | 3 |
| 22 | " | 305 | 82 | 93 | 92 | 3 | 3 |
| 23 | " | 310 | 92 | 97 | 88 | 3 | 3 |
| 24 | " | 315 | 97 | 100 | 88 | 4 | 3 |
| 25 | " | 320 | 99 | 100 | 84 | 5 | 4 |
| 26 | " | 325 | 99 | 100 | 84 | 6 | 5 |

[a]Data is basis GC analysis of crude reactor effluents. Selectivities are approximate Area % on a water and feed free basis.
[b]Adducts are moles EO/mole piperazine.
[c]Temperature in degrees Centigrade.

The following trends are discernable from the data presented:

1. BisHEP is more reactive than HEP.
2. Increased EO content of the feed decreases the amount of PIP in the reactor effluent.
3. In all cases N-ethyl piperazine byproduct formation increases with increased temperature of reaction.
4. In all cases TEDA yield is optimized near 320° C. where conversions approach 100%.

C. Bis-N-Hydroxyethyl Piperazine (BisHEP) Feedstock

Recrystalized BisHEP was evaluated as a feedstock for the preparation of TEDA using the equipment and procedures of I. As discussed above, an aqueous solution (20 wt. %) was fed to the reactor. The results are presented in Table III.

TABLE III[a]

| | | TEDA via BisHEP | | | |
|---|---|---|---|---|---|
| Ex. | TEMP[b] | CONV. | TEDA | PIP | EtPIP |
| 27 | 300 | 70 | 90 | 2 | 3 |
| 28 | 305 | 74 | 90 | 2 | 3 |
| 29 | 310 | 85 | 90 | 3 | 3 |
| 30 | 315 | 88 | 87 | 3 | 4 |
| 31 | 320 | 83 | 92 | 3 | 2 |
| 32 | 325 | 98 | 83 | 5 | 5 |

[a]Data is basis GC analysis of crude reactor effluents. Selectivities are approximate Area % on a water and feed free basis.
[b]Temperature in degrees Centigrade.

In contrast with data presented in Table II, BisHEP conversion was only 98% at 325° C. This apparent decrease in activity is probably due to inaccuracies in the G.C. analysis. In cases where BisHEP concentrations start low, for example, a 75% conversion may drop the concentration of BisHEP below detectable levels resulting in a calculated 100% conversion. This is probably the reason for apparent high activity in the low EO/PIP adducts.

Using the same procedure as outlined above, a crude BisHEP feedstock was tested as described above in I. The feed was prepared as a 1:1 EO/HEP adduct; this is expected to be equivalent to a 2:1 EO/PIP adduct. At 320° C., conversion was about 96% with a selectivity of 89% to TEDA.

D. Ethoxylated Crude Polyethylenepolyamine Feedstock

A blend was prepared to simulate a crude aminoethylethanolamine (AEEA) material obtainable by flashing material from a residue stream of an ethylenediamine plant. The composition of this blend was (by weight) 88% AEEA, 4% DETA, 4% AEP, and 4% HEP. This blend was then ethoxylated with various equivalents of EO. The feed consisted of a 20 wt. % aqueous solution of this ethoxylated material and the runs were made as described in I. The selectivity data using this feed is presented in Table IV.

TABLE IV[a]

| | | TEDA via Ethoxylated Amine C-1 | | | | |
|---|---|---|---|---|---|---|
| Ex. | Adduct | Conv[c] | TEMP[b] | TEDA | PIP | EtPIP |
| 33 | 1:1 | >95% | 320 | 61% | 10% | 9% |
| 34 | 1:1 | >99% | 330 | 70% | 9% | 15% |
| 35 | 1.5:1 | >83% | 330 | 63% | 5% | 5 |

[a]Data is basis GC analysis of crude reactor effluents. Selectivities are approximate Area % on a water and feed free basis.
[b]Temperature in degrees Centigrade.
[c]Conversions are approximate and based upon the HEP and BisHEP content.

It is readily obvious that the selectivity to TEDA using this feed mix is considerably lower than the other alternatives discussed above. However, this route uses a relatively inexpensive feedstock.

E. Ethoxylated Ethylenediamine (EO/EDA, 2:1) Feedstock

In another variation, a 2:1 (m/m) ratio of EO/EDA was used as the source of TEDA precursor. This material should be similar to the ethoxylated crude AEEA (Amine C-1 of Example B). This run was performed as described above in I using a 20% solution as feed. The temperature required for near complete conversion was 340° C. as compared to about 320° C. for the HEP feedstocks. The selectivity to TEDA at this temperature was 60%. The major byproducts were still PIP and EtPIP.

F. Diethanolamine (DEA) Feedstock

Diethanolamine was used as a feed for the preparation of TEDA. The first step involves a bimolecular cyclization to BisHEP. The BisHEP then reacts as in the above examples to give TEDA. The yield in this approach is very poor due to losses from side reactions. This suggests that the initial formation of BisHEP exhibits poor selectivity since the subsequent cyclization of BisHEP goes in high selectivity. At 320° C., DEA coversion was >95%. Selectivity to TEDA was only 40%.

Long-term Catalyst Stability Evaluations

G. HEP Process

A 1000 hour catalyst evaluation was run with 20% (v/v) aqueous HEP to determine the activity/selectivity stability over prolonged use. Operation of the run was identical to that described above in I. In this experiment the initial temperature required for 99% HEP conversion was 330° C.; selectivity to TEDA was 74%. After 800 hours on-stream, conversion was 99% with a selectivity to TEDA of 72% at an operational temperature of 340° C. After 1000 hours on-stream, conversion was 97% with a selectivity to TEDA of 67% at an operation temperature of 345° C. This represents a modest loss in activity and selectivity occuring in the last several hundred hours of operation. Regeneration of the catalyst was not attempted.

H. Ethoxylated Piperazine (EO/PIP, 1.5:1) Feedstock

A 4:1 aqueous dilution of crude HEP was prepared for this evaluation. The material contained 25% water presumable from the use of piperazine eutectic formed in the preparation of this adduct. This feed contained 25% PIP, 61% HEP, and 14% BisHEP on a water-free basis and run in the manner described above in I. As seen in runs using pure HEP, there is a net production of piperazine. Initially, on a piperazine feed-free basis, the selectivity to PIP, EtPIP, and TEDA was 7%, 11%, and 80%, respectively; 99% Conversion was obtained at 333° C. After 1000 hours, 99% conversion was obtained at 340° C.; selectivities were 4%, 19%, 69%, respectively.

I. Hydroxyethyldiethylenetriamine

A 20% aqueous solution of crude hydroxyethyldiethylenetriamine was evaluated in the manner described above in I. The run was made at 310° C. at atmospheric pressure with a LHSV of 1. On a feed-free basis, the selectivity to products was:

AEP—49.6%
PIP—11.6%
TEDA—16.1%

Conversion of the feed was 95.6%.

At 290° C., feed conversion was 65.8% and selectivities were:

AEP—65.3%
PIP—3.8%
TEDA—7.3%

The foregoing examples are given by way of illustration only and are not intended as limitations on the scope of this invention, as defined by the appended claims.

What is claimed is:

1. A method for the manufacture of triethylenediamine which comprises bringing an aqueous solution of a hydroxyethyl ethyleneamine feedstock containing about 5 to about 50 wt. % of said feedstock into contact with a cyclization catalyst at a temperature of about 300°-400° C. for a period of time sufficient to convert at least a portion of said feedstock to triethylenediamine; said feedstock being:

a. an acyclic hydroxyethyl ethyleneamine having the formula:

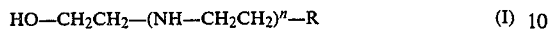

wherein R represent —OH or $NH_2$ and n is an integer having a value of 1 or 2; or b. a cyclic hydroxyethylenepolyamine having the formula:

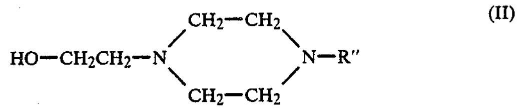

wherein R" represents H, —$CH_2CH_2OH$;

or a mixture of said acyclic hydroxyethyl ethyleneamines and said cyclic hydroxyethylenepolyamines;

c. said catalyst composition consisting essentially of titania or zirconia having from about 0.5 to about 7 wt. % of phosphorus thermally chemically bonded to the surface thereof in the form of phosphate bonds.

2. A method as in claim 1 wherein the feedstock is said acyclic polyethylenepolyamine feedstock.

3. A method as in claim 1 wherein said feedstock is said cyclic polyethylenepolyamine feedstock.

4. A method for the manufacture of triethylenediamine which comprises bringing an aqueous solution of a hydroxyethyl ethyleneamine feedstock containing about 5 to about 50% of said feedstock into contact with a cyclization catalyst at a temperature of about 300°-400° for a period of time sufficient to convert at least a portion of said feedstock to triethylenediamine;

said feedstock being an ethyoxylation product of a mixture of N-hyroxyethylpiperazine, N-aminoethylpiperazine, diethylenetriamine and aminoethylethanolamine ethyloxylated in the molar ratio of about 1 to about 1.5 moles of ethylene oxide per molar equivalent of said mixture or a bimolar ethyloxylation product of ethylenediamine, said catalyst composition consisting essentially of titania or zirconia having from about 0.5 to about 7 wt. % of phosphorus thermally chemically bonded to the surface thereof in the form of phosphate bonds.

5. A method for the continuous manufacture of triethylenediamine which comprises forming an aqueous solution of a hydroxyethyl ethyleneamine feedstock containing from about 5 to about 50 wt. % of said hydroxyethyl ethyleneamine feedstock, continuously bringing said aqueous solution into contact with a pelleted cyclization catalyst at a temperature within the range of about 300° to about 400° C., at a liquid hourly space velocity of about 0.5 to about 5 sufficient to substantially completely convert said hydroxyethyl ethyleneamine feedstock into reaction products including triethylenediamine, continuously recovering an aqueous solution of said reaction products, continuously diluting said aqueous solution with from about 5 to about 20 wt. % of propylene glycol and continuously distilling said diluted aqueous solution to obtain an azeotrope of propylene glycol and triethylenediamine in liquid form; said polyethylenepolyamine feedstock being:

a. an acyclic hydroxyethyl ethyleneamine having the formula:

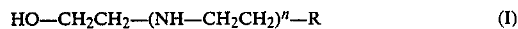

wherein R represents —OH or $NH_2$ and n is an integer having a value of 1 or 2; or b. a cyclic hydroxyethylenepolyamine having the formula:

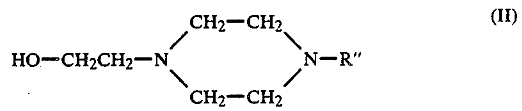

wherein R" represents H, —$CH_2CH_2OH$ or —$CH_2CH_2NH_2$;

or a mixture of said acyclic hydroxyethyl ethyleneamines and said cyclic hydroxyethylenepolyamines;

c. said catalyst composition consisting essentially of titania or zirconia having from about 0.5 to about 7 wt. % of phosphorus thermally chemically bonded to the surface thereof in the form of phosphate bonds.

6. A method as in claim 5 wherein the catalyst is a catalyst prepared by refluxing titania pellets with an aqueous solution of phosphoric or polyphosphoric acid at a temperature of about 100°-150° C. for about 0.5 to about 5 hours followed by recovery, water washing and calcining for about 2 to about 24 hours at a temperature of about 200°-800° C.

7. A method as in claim 6 wherein the feedstock is said acyclic polyethylenepolyamine feedstock.

8. A method as in claim 7 wherein said feedstock comprises aminoethylethanolamine.

9. A method as in claim 7 wherein the feedstock comprises diethanolamine.

10. A method as in claim 6 wherein the feedstock is a cyclic hydroxyethyl ethylenepolyamine feedstock.

11. A method as in claim 10 wherein the feedstock comprises hydroxyethylpiperazine.

12. A method as in claim 10 wherein the feedstock comprises bis-hydroxyethyl piperazine.

* * * * *